(12) United States Patent
Tang et al.

(10) Patent No.: US 10,825,569 B2
(45) Date of Patent: Nov. 3, 2020

(54) UNIVERSAL NON-INVASIVE BLOOD GLUCOSE ESTIMATION METHOD BASED ON TIME SERIES ANALYSIS

(71) Applicants: GLOBAL HEALTH ARK MEDICAL TECHNOLOGY (BEIJING) CO. LTD, Beijing (CN); TSINGHUA UNIVERSITY, Beijing (CN)

(72) Inventors: Fei Tang, Beijing (CN); Zhanxiao Geng, Beijing (CN); Xiaohao Wang, Beijing (CN); Yadong Ding, Beijing (CN); Zhiwei Fan, Beijing (CN)

(73) Assignees: Global Health Ark Medical Technology (Beijing) Co. Ltd, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 15/744,438

(22) PCT Filed: Oct. 31, 2017

(86) PCT No.: PCT/CN2017/108525
§ 371 (c)(1),
(2) Date: Jan. 12, 2018

(87) PCT Pub. No.: WO2018/107915
PCT Pub. Date: Jun. 21, 2018

(65) Prior Publication Data
US 2019/0295729 A1    Sep. 26, 2019

(30) Foreign Application Priority Data

Dec. 16, 2016   (CN) .......................... 2016 1 1170162

(51) Int. Cl.
*G16H 50/50*     (2018.01)
*G16H 50/70*     (2018.01)
(Continued)

(52) U.S. Cl.
CPC ............. *G16H 50/50* (2018.01); *G06F 30/20* (2020.01); *G16H 10/40* (2018.01); *G16H 50/70* (2018.01); *G06F 2111/10* (2020.01)

(58) Field of Classification Search
CPC ........ G16H 50/50; G16H 10/40; G16H 50/70; G06F 30/20; G06F 2111/10
(Continued)

(56) References Cited

U.S. PATENT DOCUMENTS 9,459,201 B2 * 10/2016 Gulati ................ A61B 5/02416
2010/0324398 A1 * 12/2010 Tzyy-Ping ......... A61B 5/14532
                                                        600/365
2012/0101351 A1    4/2012 Caduff et al.

FOREIGN PATENT DOCUMENTS

CN         103310113 A      9/2013
CN         104490403 A      4/2015
(Continued)

*Primary Examiner* — Kamini S Shah
*Assistant Examiner* — Faraj Ayoub
(74) *Attorney, Agent, or Firm* — Swanchik, Lloyd & Eisenschenk

(57) ABSTRACT

The present invention discloses a universal non-invasive blood glucose estimation method based on time series analysis, which comprises 5 steps, i.e., data input and preprocessing, features screening, establishment of single-feature model based on time series analysis, multi-feature fusion, and non-invasive blood glucose estimation. During non-invasive blood glucose estimation, new non-invasive test data is inputted, and the blood glucose estimation series is calculated using related feature information obtained through modeling, single-feature model, and multi-feature fusion model. The estimation method provided in the present invention is easy to execute, and can overcome the delay between changes of physiological parameters of human body and changes of blood glucose, and thereby can obtain more accurate non-invasive blood glucose test results. The (Continued)

estimation method is universal and is applicable to different non-invasive blood glucose monitoring methods.

7 Claims, 5 Drawing Sheets

(51) Int. Cl.
*G06F 30/20* (2020.01)
*G06F 111/10* (2020.01)
*G16H 10/40* (2018.01)

(58) Field of Classification Search
USPC .............................................................. 703/2
See application file for complete search history.

(56) References Cited

FOREIGN PATENT DOCUMENTS

| | | |
|---|---|---|
| CN | 105662434 A | 6/2016 |
| CN | 105962949 A | 9/2016 |
| CN | 106980746 A | 7/2017 |
| EP | 2544124 A1 * | 1/2013 ......... A61B 5/14532 |

* cited by examiner

UNIVERSAL NON-INVASIVE BLOOD GLUCOSE ESTIMATION METHOD BASED ON TIME SERIES ANALYSIS

CROSS REFERENCE TO RELATED APPLICATIONS

This application is a National Stage Application of International Application Number PCT/CN2017/108525, filed Oct. 31, 2017; which claims priority to Chinese Application No. 201611170162.5, filed Dec. 16, 2016.

TECHNICAL FIELD

The present invention relates to non-invasive monitoring of blood glucose in human body, belongs to the field of non-invasive blood glucose monitoring, and particularly relates to a universal non-invasive blood glucose estimation method based on time series analysis.

BACKGROUND ART

Diabetes is a group of metabolic diseases characterized by high blood glucose, and there is no radical cure to diabetes yet at present. The treatment of diabetes needs frequently monitoring glucose to control blood glucose level. The conventional invasive blood sampling method has obvious defects, causes wound and pain to the patient in the measuring process, and is inconvenient for continuous monitoring. Non-invasive blood glucose monitoring technology overcomes the drawbacks of the conventional method, which can effectively meet the demand of diabetic patients for real-time and frequent monitoring of blood glucose concentration. Non-invasive method is the developing direction of blood glucose monitoring technology. However, the accuracy of current non-invasive blood glucose method can't meet the requirement yet.

The present non-invasive blood glucose estimation method is to obtain the glucose value according to physiological parameters at the time of testing. For example, in US Patent No. US20120101351A1, the characteristic of impedance spectrum measured at the time of test is utilized to estimate the blood glucose; in Chinese Patent No. CN105662434A, the characteristic of mid-infrared light measured at the time of test is utilized to estimate the blood glucose; in Chinese Patent No. CN104490403A, spectral information obtained at the time of test is utilized to estimate the blood glucose.

A Chinese patent document (CN103310113A) has disclosed a method that utilizes the potential time series dynamic characteristic of blood glucose to estimate the blood glucose. That method utilizes subcutaneous blood glucose level measured some time ago with an invasive method to predict the blood glucose later. That method belongs to a technique that utilizes the dynamic variation characteristic of blood glucose in human body and uses the blood glucose level acquired some time ago with an invasive method to predict the blood glucose later.

Non-invasive blood glucose method estimates blood glucose by testing physiological parameters of human body related with blood glucose level; however, there is a time delay between changes in glucose and changes in physiological parameters, and the time delay may vary from one physiological parameter to another; therefore, the present blood glucose can't be estimated simply with present physiological parameters. Using historical blood glucose information to predict blood glucose, though time series of blood glucose are used, the historical blood glucose has to be acquired with an invasive method. Consequently, the wound and infection risk incurred by an invasive method can't be avoided.

CONTENTS OF THE INVENTION

To overcome the drawbacks in the existing non-invasive blood glucose estimation method, the present invention utilizes time series analysis method to establish a blood glucose estimation model, overcome the time delay between changes in physiological parameters and changes in blood glucose level.

The technical scheme of the present invention is as follows:

A universal non-invasive blood glucose estimation method based on time series analysis, characterized in that the method comprises the following steps:

1) data input and preprocessing: acquiring relevant physiological parameters of human body continuously with a non-invasive method to obtain a feature value sequence $x_i(t)$, $i=1, \ldots, T$, $t=1, \ldots, Z$, where, i is the serial number of feature value, t is the serial number of sampling site, T is the number of feature values obtained through calculation of the acquired physiological parameters, and Z is the length of the series; at the same time, using an invasive method to get the reference blood glucose level series Glu(t), and normalizing the feature value sequence and the reference blood glucose level sequence;

2) features screening: features were screened according to the similarity between the feature value and the reference blood glucose level sequence, a subset of features that are highly related with of the reference blood glucose was selected, and recorded in related features information;

3) establishing single-feature model based on time series analysis: expressing the relation between each of the related features and the reference blood glucose level sequence with a time series analysis model, to obtain single-feature model and single-feature model-based glucose profiles;

4) multi-feature fusion: single-feature model-based glucose profiles were integrated using the weighted average method, and then multi-feature model were obtained;

5) carrying out non-invasive blood glucose estimation with the information of the related features, the single-feature model, and the multi-feature fusion model.

The universal non-invasive blood glucose estimation method based on time series analysis in the above scheme is characterized in that: in the features screening in the step 2), the similarity between the feature value sequence and the reference blood glucose level sequence is obtained with a cross-correlation function. For the feature value sequence $x_i(t)$, the function of correlation with the reference blood glucose level sequence is:

$$R(\tau) = \sum_{t=0}^{N-1}(x_i(t)Glu(t+\tau))/N$$

where, N is the set length of calculated cross-correlated series, $R(\tau)$ is the value of the cross-correlation function, and $\tau$ is the independent variable of the cross-correlation function; during the features screening, if the maximum value $R_{max}$ of $R(\tau)$ exceeds a preset threshold, the two series will be deemed as being similar to each other, and the feature will be selected as a related feature and added into the subset of related features; in the subset of related features, the total number of related features is M, and the serial number of related features is j.

The universal non-invasive blood glucose estimation method based on time series analysis in the above scheme is characterized in that: in the establishment of single-feature model based on time series analysis in the step 3), the relation between the related features and the reference blood glucose level sequence is expressed with a moving average model in the time series analysis method, as follows:

$$Glu(t) = \sum_{n=0}^{m-1} x_j(t-n) \times b_{jn} + \varepsilon_j(t)$$

where, m is the order of the model, $0 \leq n < m$, $b_{jn}$ is a coefficient of the model, and $\varepsilon_j(t)$ is residual error;

The coefficient $b_{jn}$ of the model is obtained with the least square method, and thereby an intermediate variable $g_j(t)$ is obtained:

$$g_j(t) = \sum_{n=0}^{m-1} x_j(t-n) \times b_{jn}$$

From $g_j(t)$ and $Glu(t)$, the delay $T_j$ between them is obtained, and finally a blood glucose sequence $G_j(t)$ based on the single-feature model is obtained:

$$G_j(t) = g_j(t - T_j)$$

The universal non-invasive blood glucose estimation method based on time series analysis in the above scheme is characterized in that: during the multi-feature fusion in the step 4), a weighted average model is used for the fusion to obtain a parameter $K_j$ of the multi-feature model ($K_j$ is a corresponding weight factor of $G_j(t)$), and then the following formula is obtained with a linear regression model:

$$Glu(t) = \sum_{n=0}^{m-1} x_j(t-n) \times b_{jn} + \varepsilon_j(t)$$

The universal non-invasive blood glucose estimation method based on time series analysis in the above scheme is characterized in that: the non-invasive blood glucose estimation carried out in the step 5) specifically comprises the following steps:

1) acquiring relevant physiological parameters of human body continuously with a non-invasive method to retrieve a feature value sequence $x_i(t)$, and preprocessing the feature value sequence;
2) extracting related features with the related feature information obtained in the modeling step 2) to obtain a subset of related features, in which the total number of related features is M, and the serial number of related features is j;
3) carrying out single-feature model estimation according to the parameters m, $b_{jn}$ and $T_h$ of the single-feature model obtained in the modeling step 3), to obtain $g_j(t)$ and $G_j(t)$, where, $$g_j(t) \sum_{n=0}^{m-1} x_j(t-n) \times b_{jn}$$

4) the final estimated blood glucose sequence is obtained according to the parameter $K_j$ of the multi-feature model obtained in the modeling step 4):

$$G(t) = \sum_{j=1}^{M} G_j(t) \times K_j.$$

The universal non-invasive blood glucose estimation method based on time series analysis in the above scheme is characterized in that: the physiological parameters acquired non-invasively include infrared spectrum feature, impedance feature, temperature, humidity, blood flow velocity, blood oxygen saturation degree, pulse, acoustic velocity, acoustic impedance, and photoacoustic spectrum feature.

The universal non-invasive blood glucose estimation method based on time series analysis in the above scheme is characterized in that: the feature sequence and the reference blood glucose level sequence are filtered by wavelet filtering after they are normalized in the preprocessing procedure.

Compared with the prior art, the present invention has the following advantages and prominent effects: (1) the universal non-invasive blood glucose estimation method based on time series analysis provided in the present invention is simple and easy to use, and it can establish a model for each diabetic patient simply through a test of about three hours; (2) the method eliminates the delay between changes of physiological parameters and changes of blood glucose concentration, and can obtain more accurate blood glucose levels with a non-invasive method; (3) the method provided in the present invention is applicable to a variety of different non-invasive blood glucose testing methods and is universal.

EMBODIMENTS

Hereunder the specific process of the universal non-invasive blood glucose estimation method based on time series analysis provided in the present invention will be further detailed with reference to the accompanying drawings.

1. Example 1

Now the specific process of the universal non-invasive blood glucose estimation method based on time series analysis will be further detailed in conjunction with a multi-sensor non-invasive blood glucose monitor based on an impedance spectroscopy-optical method.

Figure 8:
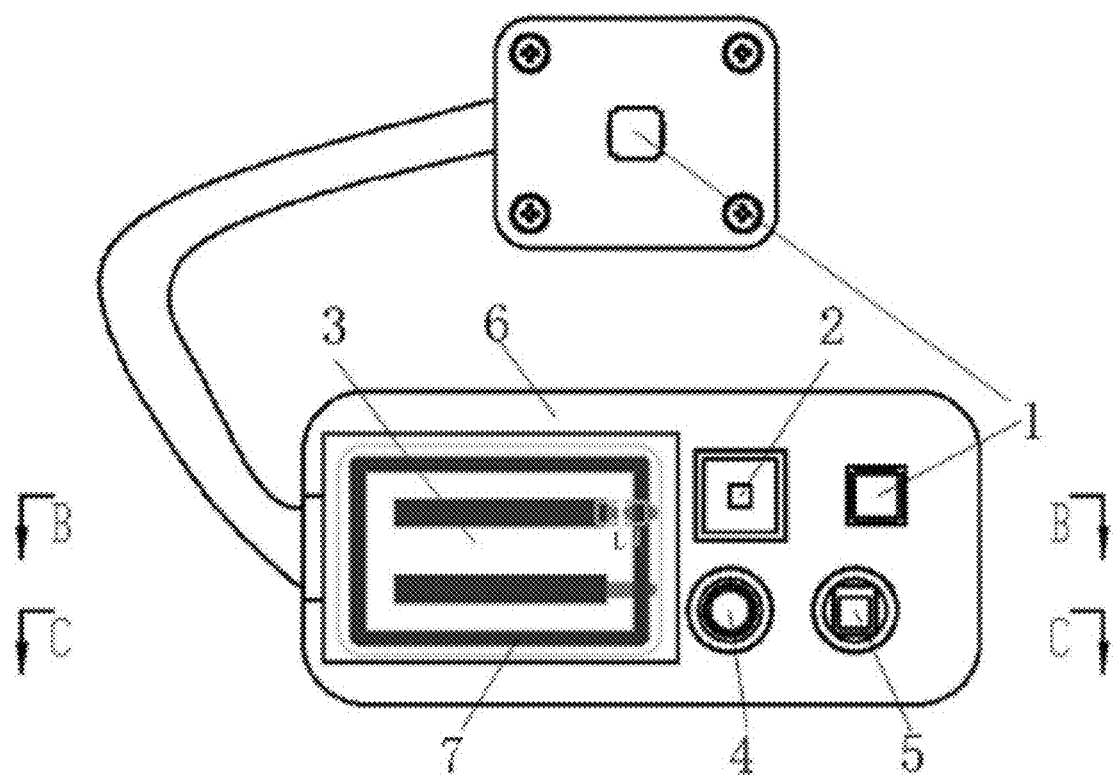
FIG. 8 shows the probe of a multi-sensor non-invasive blood glucose tester based on an impedance spectroscopy-optical method.
In the figures: 1—low-frequency electrodes; 2—temperature and humidity sensor, 3—high-frequency electrodes; 4—LED array; 5—photoelectric sensor; 6—contact plate; 7—shielding electrode; L—matching inductor of high-frequency electrodes

The test probe of a multi-sensor non-invasive blood glucose tester based on impedance spectroscopy-optical method is shown in FIG. 8, and comprises a temperature and humidity sensor 2, an LED array 4, a photoelectric sensor 5, a pair of low-frequency electrodes 1, and a pair of high-frequency electrodes 3. The high-frequency electrodes employ parallel electrodes, a matching inductor is directly soldered to the positive pole or negative pole of the electrodes, and the high-frequency electrodes are provided with a shielding electrode 7. The low-frequency electrodes are located at 15 cm from the testing site, and can measure the low-frequency impedance of the tissue stably.

Figure 6:
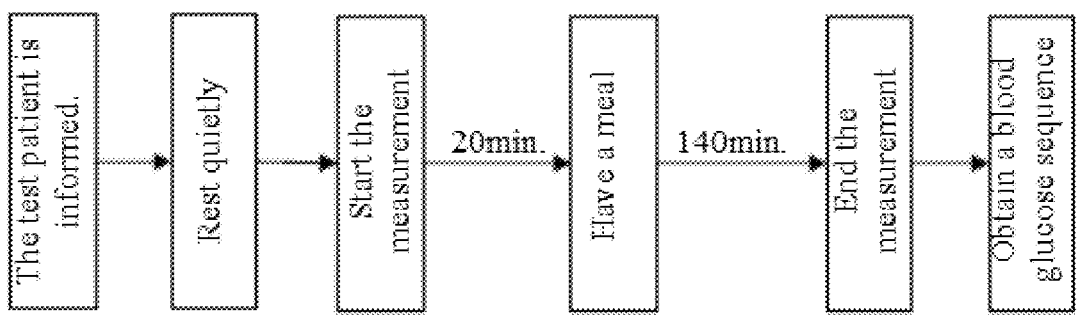
FIG. 6 is a flow diagram of data acquisition.

First, data acquisition is carried out with the multi-sensor non-invasive blood glucose monitor based on impedance spectroscopy-optical method. The data acquisition process is shown in FIG. 6, and specifically comprises the following steps:
1) The test patient begins test with an empty stomach, and shall not do any strenuous exercise within 30 minutes before the test; preferably the test patient sits still in a comfortable gesture in a comfortable environment before the test.
2) The test patient wears the non-invasive monitor, and information of relevant physiological parameters of the test patient is continuously acquired. Here, the non-invasive monitor may be any tester based on any principle.
3) The test patient has a meal after he/she has worn the non-invasive tester for 20 minutes, and finishes the meal within 15 minutes; preferably the quantity of the meal is controllable.
4) The data is acquired continuously for at least 140 minutes after the meal. Preferably the data within 3 h after the meal is acquired, so that the entire process of blood glucose increase and decrease after the meal can be obtained. The acquired data length doesn't have to be the same for each test.

While the data is acquired with the non-invasive tester, the reference blood glucose level is obtained with an invasive method; for example, the data of fingertip blood may be acquired once every 30 minutes, to obtain a reference blood glucose level sequence Glu(t).

The non-invasive blood glucose monitor based on impedance spectroscopy-optical method needs to collect the variations of the tissue features, including low-frequency impedance, high-frequency impedance, temperature, humidity, and light-transmittance, etc., over time.

Each parameter is calculated once every 1 minute, and the data is stored in a file.

After the data acquisition, modeling is carried out with the acquired data, through the following steps:
1) data input and preprocessing: relevant physiological parameters of human body, including low-frequency impedance, high-frequency impedance, resonant frequency, temperature, humidity, and light-transmittance of tissue, etc., are acquired continuously with the non-invasive method, and a feature value sequence $x_i(t)$ (i=1, . . . , T) are obtained through calculation with the physiological parameters, where, T is the total number of feature value points, and is determined as 10 for the impedance spectroscopy-optical method, and $x_i(t)$ is the time series value of the ith feature value. The reference blood glucose level sequence Glu(t) obtained with a conventional method are inputted. The feature value sequence and the reference blood glucose level sequence are normalized. In addition, interpolation is carried out in the feature value sequence and the reference blood glucose level sequence, to obtain a time matching feature value sequence and the reference blood glucose level sequence.

Figure 1:
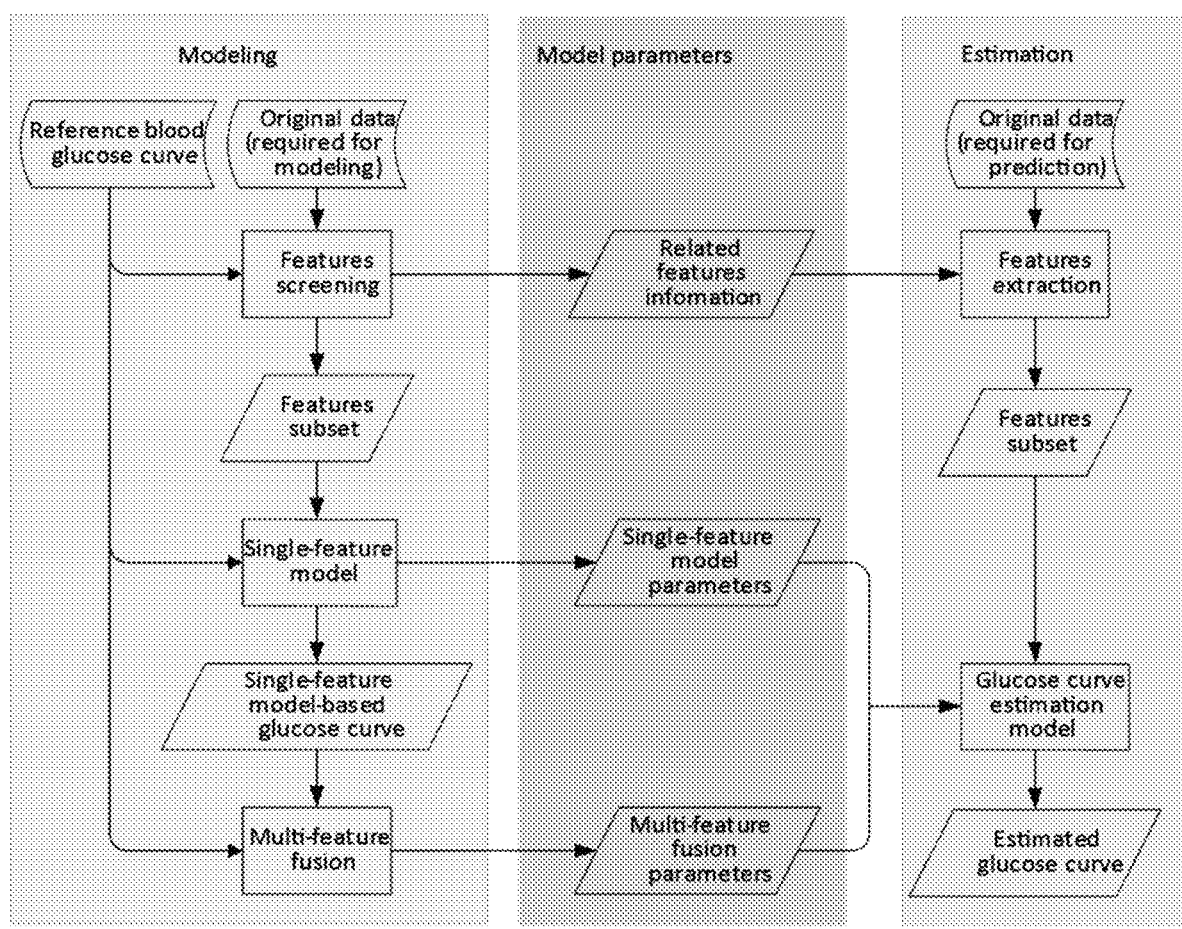
FIG. 1 is a block flow diagram of the universal non-invasive blood glucose estimation method based on time series analysis.
Figure 2:
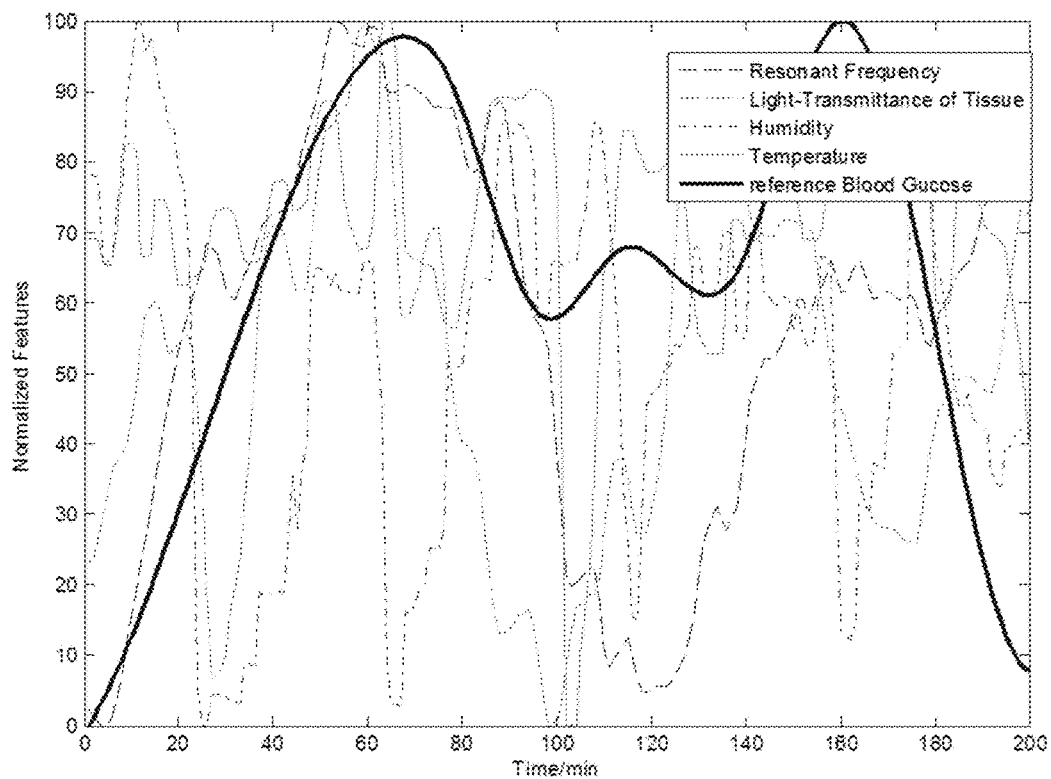
FIG. 2 shows examples of the feature value sequence obtained non-invasively and the reference blood glucose level sequence.

Examples of normalization of a feature value sequence and a reference blood glucose level sequence are shown in FIG. 2. The FIG. 2 shows the normalization results of a series of parameters (resonant frequency of the tissue, light-transmittance, temperature, and humidity) and a reference blood glucose level sequence.

Figure 3:
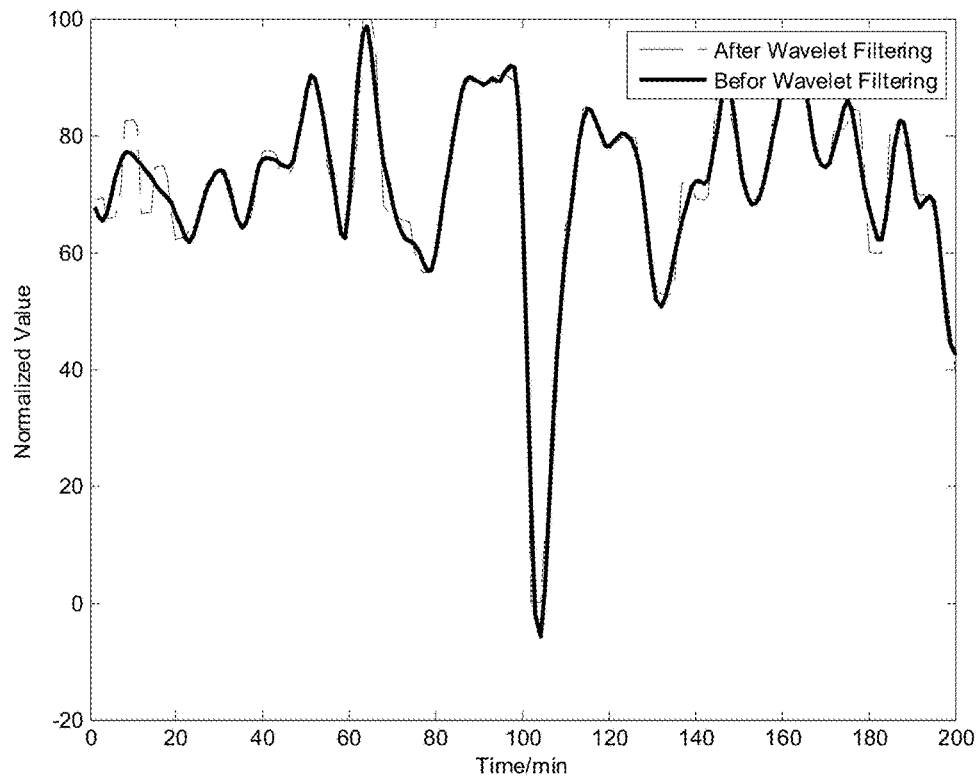
FIG. 3 shows an example of wavelet filtering result.

To eliminate high frequency noise, the raw time series is filtered by wavelet filtering. First, a wavelet basis is selected for wavelet filtering. Here, db8 wavelet may be used. The raw signals are decomposed in six layers, and the first layer and the second layer are reconstructed to eliminate high frequency noise. The effect of wavelet filtering is shown in FIG. 3.

2) features screening: a subset of features that are highly related with of the reference blood glucose are selected according to the similarity between the feature value sequence and the reference blood glucose level sequence, and the information of the related features is recorded; the similarity between the feature value sequence and the reference blood glucose level sequence is obtained with a cross-correlation function. For the feature value sequence $x_i(t)$, the function of correlation with the reference blood glucose level sequence is:

$$R(\tau) = \sum_{t=0}^{N-1} (x_i(t)Glu(t+\tau))/N \qquad (1)$$

where, N is the set length of calculated cross-correlated series, $R(\tau)$ is the value of the cross-correlation function, and $\tau$ is the independent variable of the cross-correlation function. During the features screening, if the maximum value $R_{max}$ of $R(\tau)$ exceeds a preset threshold, the two signals will be deemed as being similar to each other, and the feature will be taken as a related feature and added into the subset of related features; in the subset of related features, the total number of related features is M, and the serial number of related features is j.

3) establishing single-feature model based on time series analysis: the relation between the related feature value sequence and the reference blood glucose level sequence is expressed with a moving average model in the time series analysis method, as shown in the following formula:

$$Glu(t) = \sum_{n=0}^{m-1} x_j(t-n) \times b_{jn} + \varepsilon_j(t) \qquad (2)$$

where, m is the order of the model, 0≤n<m, $b_{jn}$ is a coefficient of the model, and $\varepsilon_j(t)$ is residual error;

The coefficient $b_{jn}$ of the model is obtained with the least square method, and thereby an intermediate variable $g_j(t)$ is obtained:

$$g_j(t) = \sum_{n=0}^{m-1} x_j(t-n) \times b_{jn} \qquad (3)$$

From $g_j(t)$ and Glu(t), the delay $T_j$ between them is obtained, and finally a blood glucose sequence $G_j(t)$ based on the single-feature model is obtained:

$$G_j(t) = g_j(t - T_j) \qquad (4)$$

The delay $T_j$ between $g_j(t)$ and Glu(t) may be obtained with a cross-correlation function as shown in formula (5):

$$R(\tau) = \sum_{t=0}^{N-1} (g_j(t) Glu(t+\tau))/N \qquad (5)$$

where, N is the set length of calculated cross-correlated series, $R(\tau)$ is the value of the cross-correlation function, and $\tau$ is the independent variable of the cross-correlation function. The $\tau$ value corresponding to the maximum value $R_{max}$ of the cross-correlation function is $T_j$.

Figure 4:
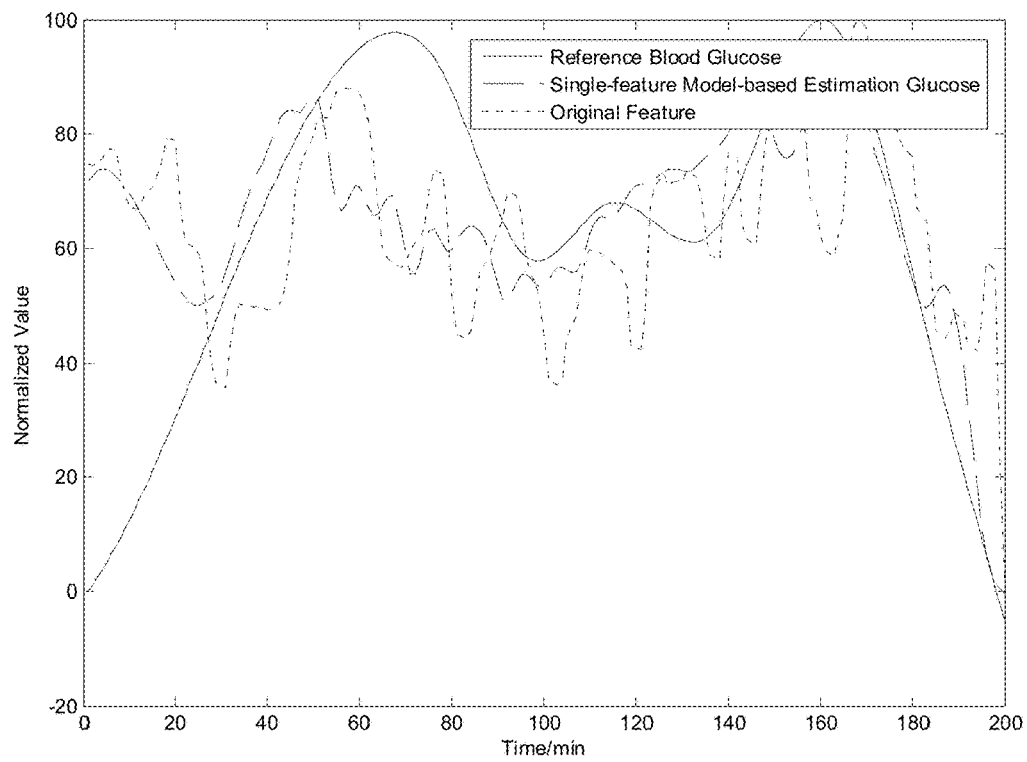
FIG. 4 shows an example of the result of a single-feature model.

Here, the order of the model may be set to 10; the estimated glucose result of a single-feature model is shown in FIG. 4, in which the relation between the reference blood glucose level sequence, the raw features, and the single-feature model estimated blood glucose is shown.

The non-invasive blood glucose test predicts blood glucose by testing physiological parameters of human body related with blood glucose level; however, there is some delay between changes of blood glucose in human body and changes of physiological parameters of human body, and the delay may be different for different physiological parameters; therefore, the present blood glucose can't be estimated simply with present physiological parameters.

Here, a model is established with a time series analysis method to overcome the time delay between changes of physiological parameters and changes of blood glucose.

Figure 5:
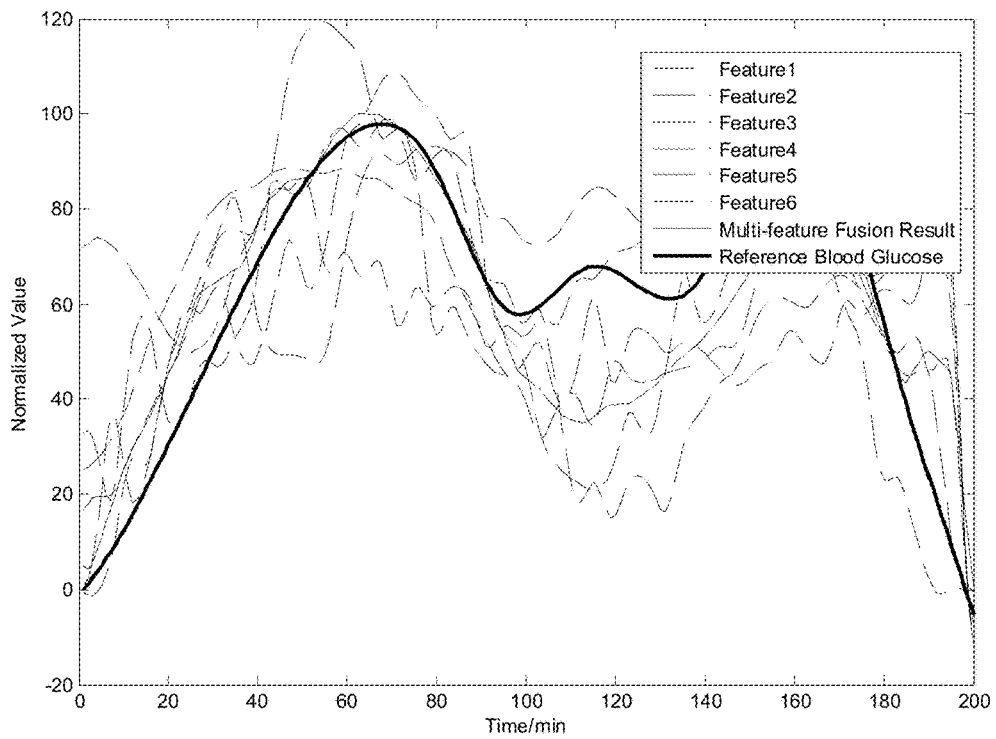
FIG. 5 shows comparison between the results of the single-feature model and the result of the multi-feature model.

4) multi-feature fusion: A weighted average model is used for the fusion of the blood glucose sequence in the single-feature model to obtain a parameter of the multi-feature model, and the weight factor $K_j$ corresponding to $G_j(t)$ is obtained with a linear regression model:

$$Glu(t) = \sum_{j=1}^{M} G_j(t) \times K_j + \varepsilon(t) \qquad (6)$$

where, $\varepsilon(t)$ is residual error,

After the $K_j$ is obtained, a blood glucose sequence based on the multi-feature model are obtained by weighted averaging:

$$G(t) = \sum_{j=1}^{M} G_j(t) \times K_j \qquad (7)$$

where, G(t) is the blood glucose sequence based on the multi-feature model;

The blood glucose sequence based on the multi-feature model are better than that on a signle-feature model, because the former integrates the information of all features, and thereby can obtain a more stable estimated result, as shown in FIG. 5.

5) carrying out non-invasive blood glucose estimation with the established models:
1) acquiring relevant physiological parameters of human body continuously with a non-invasive method to obtain a new feature value sequence $x_i(t)$, and preprocessing the feature value sequence;
2) extracting related features with the related features information obtained in the modeling step 2) to obtain a subset of related features, in which the total number of related features is M, and the serial number of related features is j;
3) canying out single-feature model estimation according to the parameters m, $b_{jn}$, and $T_j$ of the single-featuree model obtained in the modeling step 3), to obtain $g_j(t)$ and $G_j(t)$, where, $$g_j(t) = \sum_{n=0}^{m-1} x_j(t-n) \times b_{jn},$$

$$G_j(t) = g_j(t - T_j);$$

4) the final estimated blood glucose sequence is obtained according to the parameter $K_j$ of the multi-feature model obtained in the modeling step 4):

$$G(t) = \sum_{j=1}^{M} G_j(t) \times K_j.$$

Figure 7:
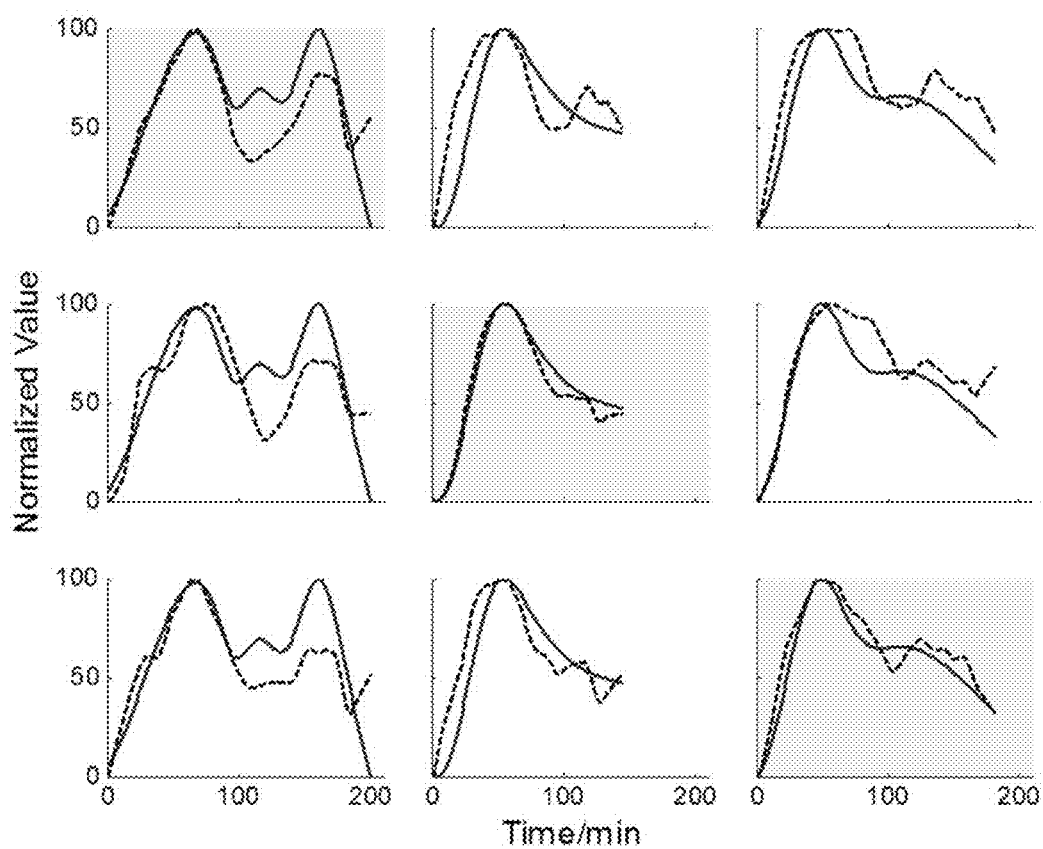
FIG. 7 shows an example of blood glucose estimation result.

The result of blood glucose estimation obtained with the above-mentioned method is shown in FIG. 7. A user is tested for 3 times, modeling is carried out with the data in one test, and then the results of the other two tests are estimated. In the figure, the pictures in a gray background represent the modeling result, while the pictures in a white background represent the estimated results. The dotted lines in the pictures represent estimated results, while the solid lines in the pictures represent reference blood glucose results. It is seen that the result of blood glucose estimated with the method is accurate.

From the above process, it can be seen that, the models can be established simply through one test, and the entire process takes about three hours. Different features can be obtained with different test methods, while the modeling method remains unchanged. Therefore, the method is universal. The spectral characteristics of the tissue, such as mid-infrared band, near-infrared band, and visible light band, etc., may be acquired non-invasively with an optical method. Acoustic features of the tissue can be acquired non-invasively with an ultrasonic method, and then features such as acoustic velocity and acoustic impedance, etc., may be extracted.

The invention claimed is:
1. A non-invasive blood glucose estimation method based on time series analysis, the method comprising:

a) a data input and preprocessing step, comprising:
  i) acquiring, using a multi-sensor non-invasive blood glucose monitor, first physiological parameters of a human body continuously;
  ii) calculating, by a processor in operable communication with the multi-sensor non-invasive blood glucose monitor, a feature value sequence $x_i(t)$ from the first physiological parameters, where i is an integer serial number of a respective feature and ranges from 1 to T, t is an integer serial number of a sampling point and ranges from 1 to Z, T is a total number of features calculated from the first physiological parameters, and Z is a length of the feature value sequence;
  iii) at the same time as the first physiological parameters are acquired using the multi-sensor non-invasive blood glucose monitor, using an invasive sensor device to extract blood from the human body and obtain a reference blood glucose level series Glu(t); and
  iv) normalizing the feature value sequence $x_i(t)$ and the reference blood glucose level series Glu(t);
b) calculating, by the processor, a correlation subset of features from $x_i(t)$ that are correlated to the reference blood glucose level series Glu(t) using a cross-correlation function;
c) expressing, by the processor, a relation between each feature of the correlation subset and the reference blood glucose level series Glu(t) with a time series analysis model, to obtain a single-feature model and a plurality of single-feature model-based glucose profiles;
d) integrating, by the processor, the single-feature model-based glucose profiles using a weighted average method, to obtain a multi-feature fusion model; and
e) estimating, by the processor, a blood glucose level of the human body non-invasively based on the correlation subset, the single-feature model, and the multi-feature fusion model.

2. The method according to claim 1, wherein the cross correlation function is:

$$R(\tau) = \sum_{t=0}^{N-1} (x_i(t) Glu(t+\tau))/N$$

where N is a set length of a calculated cross-correlated series, $R(\tau)$ is a value of the cross-correlation function, and $\tau$ is an independent variable of the cross-correlation function,
  wherein during the calculating of the correlation subset, if a maximum value $R_{max}$ of $R(\tau)$ exceeds a preset threshold, the respective feature will be added to the correlation subset, and wherein a total number of features in the correlation subset is M, and an integer serial number of features in the correlation subset can be represented as j.

3. The method according to claim 1, wherein the time series analysis model is a moving average model expressed as follows:

$$Glu(t) = \sum_{n=0}^{m-1} x_j(t-n) \times b_{jn} + \varepsilon_j(t)$$

where m is an order of the moving average model, 0≤n<m, $b_{jn}$ is a coefficient of the moving average model, and $\varepsilon_3(t)$ is a residual error of the moving average model,
  wherein $b_{jn}$ is obtained with a least square method including calculation of an intermediate variable $g_j(t)$ as follows:

$$g_j(t) = \sum_{n=0}^{m-1} x_j(t-n) \times b_{jn},$$

and
  wherein the single-feature model is $G_3(t)$ and is calculated as follows:

$$G_j(t) = g_j(t - T_j)$$

where $T_j$ is a delay between $g_j(t)$ and Glu(t).

4. The method according to claim 1, wherein the weighted average method comprises using a weighted average model to obtain a parameter $K_j$ of the multi-feature fusion model, where $K_j$ is a corresponding weight factor of $G_j(t)$, and then using a linear regression model as follows:

$$Glu(t) = \sum_{j=1}^{M} G_j(t) \times K_j + \varepsilon(t),$$

where $\varepsilon(t)$ is a residual error.

5. The method according to claim 1, wherein the estimating of the blood glucose level of the human body non-invasively carried out in the step e) comprises the following sub-steps:
  i) acquiring second physiological parameters of the human body continuously and non-invasively to calculate an estimation feature value sequence $x_i(t)$ from the second physiological parameters, and preprocessing the estimation feature value sequence;
  ii) extracting the features that are correlated to the reference blood glucose level series Glu(t) using the correlation subset obtained in step b) to obtain a subset of related features, in which a total number of related features is M, and a serial number of related features is j;
  iii) carrying out a single-feature model estimation according to parameters m, $b_{jn}$, and $T_j$ of the single-feature model obtained in step c), to obtain $g_j(t)$ and $G_j(t)$, where $$g_j(t) = \sum_{n=0}^{m-1} x_j(t-n) \times b_{jn}, \text{ and } G_j(t) = g_j(t - T_j);$$

and
  iv) obtaining a final estimated blood glucose sequence according to a parameter $K_j$ of the multi-feature fusion model obtained in step d) as follows:

$$G(t) = \sum_{j=1}^{M} G_j(t) \times K_j,$$

wherein the time series analysis model is a moving average model expressed as follows:

$$Glu(t) = \sum_{n=0}^{m-1} x_j(t-n) \times b_{jn} + \varepsilon_j(t),$$

where m is an order of the moving average model, $0 \leq n < m$, $b_{jn}$ is a coefficient of the moving average model, and $\varepsilon_j(t)$ is a residual error of the moving average model, and wherein the weighted average method comprises using a weighted average model to obtain the parameter $K_j$ of the multi-feature fusion model, where $K_j$ is a corresponding weight factor of $G_j(t)$, and then using a linear regression model as follows:

$$Glu(t) = \sum_{j=1}^{M} G_j(t) \times K_j + \varepsilon(t),$$

where $\varepsilon(t)$ is a residual error.

6. The method according to claim 1, wherein the physiological parameters comprise an infrared spectrum feature, an impedance feature, a temperature, a humidity, a blood flow velocity, a blood oxygen saturation degree, a pulse, an acoustic velocity, an acoustic impedance, and a photoacoustic spectrum feature.

7. The method according to claim 1, wherein step a) further comprises, after substep iv), wavelet filtering the feature value sequence $x_i(t)$ and the reference blood glucose level series Glu(t).

* * * * *